US 11,203,161 B2

(12) United States Patent
Baker (10) Patent No.: US 11,203,161 B2
(45) Date of Patent: Dec. 21, 2021

(54) METHODOLOGY FOR RAPID ADDITIVELY MANUFACTURED TITANIUM STRENGTH ASSESSMENT UTILIZING ELECTRICAL RESISTIVITY

(71) Applicant: The Boeing Company, Chicago, IL (US)

(72) Inventor: Andrew H. Baker, Everett, WA (US)

(73) Assignee: The Boeing Company, Chicago, IL (US)

( * ) Notice: Subject to any disclaimer, the term of this patent is extended or adjusted under 35 U.S.C. 154(b) by 353 days.

(21) Appl. No.: 16/457,234

(22) Filed: Jun. 28, 2019

(65) Prior Publication Data

US 2020/0406556 A1 Dec. 31, 2020

(51) Int. Cl.
| | |
|---|---|
| *B29C 64/393* | (2017.01) |
| *G01N 27/04* | (2006.01) |
| *G01N 27/14* | (2006.01) |
| *B33Y 40/00* | (2020.01) |
| *B33Y 50/00* | (2015.01) |

(52) U.S. Cl.
CPC ......... *B29C 64/393* (2017.08); *G01N 27/041* (2013.01); *G01N 27/14* (2013.01); *B33Y 40/00* (2014.12); *B33Y 50/00* (2014.12)

(58) Field of Classification Search
CPC .... B29C 64/393; G01N 27/041; G01N 27/14; B33Y 40/00; B33Y 50/00
See application file for complete search history.

(56) References Cited

U.S. PATENT DOCUMENTS

| | | | | |
|---|---|---|---|---|
| 2018/0095450 A1* | 4/2018 | Lappas | ................... | B33Y 10/00 |
| 2018/0143147 A1* | 5/2018 | Milner | ................... | B33Y 99/00 |
| 2020/0049415 A1* | 2/2020 | Schiffres | ................ | B33Y 10/00 |
| 2020/0327267 A1* | 10/2020 | Collins | ................... | B22F 10/32 |

OTHER PUBLICATIONS

Popovic et al., "Characterization of microstructural changes in an Al-6.5wt.% Mg alloy by electrical resistivity measurements," Materials Science and Engineering A, vol. 492, Sep. 2008, 8 pages.

(Continued)

*Primary Examiner* — Yung-Sheng M Tsui
*Assistant Examiner* — Melody Tsui
(74) *Attorney, Agent, or Firm* — Yee & Associates, P.C.

(57) ABSTRACT

Assessing material strength for additive manufacturing is provided. The method comprises calibrating a baseline electrical resistivity of a multi-phase additive material for a set dislocation density as a function of phase fraction and phase composition, wherein individual phases of the material have different electrical resistivity values. After the additive material has undergone a number of heating and cooling cycles during additive manufacturing the additive material is characterized for phase fraction, phase composition, and electrical resistivity. Dislocation density of the additive material is then determined according to electrical resistivity after additive manufacturing, accounting for effects of phase fraction and phase composition determined by characterization.

20 Claims, 5 Drawing Sheets

(56) References Cited

OTHER PUBLICATIONS

Ventura et al., "Mechanical Properties and Microstructural Characterization of Cu-4.3 PCT Sn Fabricated by Selective Laser Melting," Metallurgical and Materials Transactions A: Physical Metallurgy & Materials Science, ASM International, vol. 48, No. 1, Oct. 2016, 10 pages.
Yulianto et al., "Evaluation of Changes in Dislocation Density in Tl-CP2 in the Process of Quasi-Static Loading Using Electrical Resistance Measurements" International Journal of Fracture, Kluwer Academic Publishers, vol. 175, No. I, Mar. 2012, 6 pages.
Khodabakhshi et al., "The effect of constrained groove pressing on grain size, dislocation density and electrical resistivity of low carbon steel," Materials and Design, London, vol. 32, No. 6, Feb. 2011, 7 pages.
Kumar et al., "Electrical 1-15 Conductivity, Thermal Stability, and Lattice Defect Evolution During Cyclic Channel Die Compression of OFHC Copper," Journal of Materials Engineering and Performance, ASM International, vol. 24, No. 2, Dec. 2014, 11 pages.
European Patent Office Extended Search Report, dated Oct. 16, 2020, regarding Application No. 20175660.8, 10 pages.
Hayes et al., "Predicting tensile properties of Ti-6Al-4V produced via directed energy deposition," Acta Materialia, vol. 133, Jul. 2017, pp. 120-133. https://doi.org/10.1016/j.actamat.2017.05.025.

\* cited by examiner

METHODOLOGY FOR RAPID ADDITIVELY MANUFACTURED TITANIUM STRENGTH ASSESSMENT UTILIZING ELECTRICAL RESISTIVITY

BACKGROUND INFORMATION

1. Field

The present disclosure relates generally to additive manufacturing and more specifically to using microstructural characterization and electrical resistivity to determine dislocation density in additively manufactured metal.

2. Background

A dislocation is a defect or irregularity such as a termination of a plane of atoms within a crystal structure. This defect causes surrounding planes of atoms to bend around the edge of the terminating plane. Dislocations influence several properties of the material including strength. Dislocation density is the number of dislocations in a unit of volume for crystalline material.

Increasing dislocation density in materials increases yield strength. Strengthening by dislocation density for wrought materials is imparted through mechanical cycling such as rolling or forging. In such applications, dislocation density can be determined by tracking the amount of mechanical deformation performed. However, in the case of additive manufacturing, the material in question undergoes thermal cycling instead of mechanical cycling.

SUMMARY

An illustrative embodiment provides a method of assessing material strength for additive manufacturing is provided. The method comprises calibrating a baseline electrical resistivity of a multi-phase additive material for a set dislocation density as a function of phase fraction and phase composition, wherein individual phases of the material have different electrical resistivity values. After the additive material has undergone a number of heating and cooling cycles during additive manufacturing the additive material is characterized for phase fraction, phase composition, and electrical resistivity. Dislocation density of the additive material is then determined according to electrical resistivity after additive manufacturing, accounting for effects of phase fraction and phase composition determined by characterization.

Another illustrative embodiment provides a system for assessing material strength for additive manufacturing. The system comprises a bus system; a storage device connected to the bus system, wherein the storage device stores program instructions; and a number of processors connected to the bus system, wherein the number of processors execute the program instructions to: calibrate a baseline electrical resistivity of a multi-phase additive material for a set dislocation density as a function of phase fraction and phase composition, wherein individual phases of the material have different electrical resistivity values; characterize the additive material for phase fraction, phase composition, and electrical resistivity after the additive material has undergone a number of heating and cooling cycles during additive manufacturing; and determine dislocation density of the additive material according to electrical resistivity after additive manufacturing, accounting for effects of phase fraction and phase composition determined by characterization.

Another illustrative embodiment provides a computer program product for assessing material strength for additive manufacturing. The computer program product comprises a non-volatile computer readable storage medium having program instructions embodied therewith, the program instructions executable by a number of processors to cause the computer to perform the steps of: calibrating a baseline electrical resistivity of a multi-phase additive material for a set dislocation density as a function of phase fraction and phase composition, wherein individual phases of the material have different electrical resistivity values; characterizing the additive material for phase fraction, phase composition, and electrical resistivity after the additive material has undergone a number of heating and cooling cycles during additive manufacturing; and determining dislocation density of the additive material according to electrical resistivity after additive manufacturing, accounting for effects of phase fraction and phase composition determined by characterization.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

The illustrative examples recognize and take into account different considerations. For example, the illustrative examples recognize and take into account that a significant contribution to yield strength of additively manufactured metals, such as titanium, is derived from dislocation density introduced to the material through thermal cycling inherent to rapid heating and cooling cycles of additive manufacturing (AM) processes. However, dislocation density imparted by thermal cycling in AM is not as easily determined as with mechanical deformation of wrought materials.

The illustrative embodiments also recognize and take into account that rapid qualification methodologies based on microstructure can use microstructural measurements as a way to reduce mechanical testing. In order to be useful, measurements of microstructure must have some level of fidelity, be timely, and be cost effective. For example, transmission electron microscopy (TEM) methods are excellent for qualitative assessment of titanium alloy but only capable of quantitatively assessing dislocation density within an order of magnitude above a certain threshold. Furthermore, TEM methods are expensive, time-consuming, and destructive measurements. Similarly, X-ray diffraction is another useful method but also has accuracy and resolution limitations and requires a flat specimen.

The illustrative embodiments also recognize and take into account that electrical resistivity measurements offer a relatively quick and inexpensive way to determine microstructural input for AM produced titanium alloy non-destructively.

Thus, the illustrative embodiments provide a method of microstructural characterization along with electrical resistivity as an assessment technique for additively manufactured metal such as titanium to determine the dislocation density as part of a combined approach to assess yield strength. Electrical resistivity is calibrated for a multi-phase additive material having a set dislocation density as a function of phase fraction and phase composition. After undergoing a number of AM heating and cooling cycles, the material is characterized for phase fraction, phase composition, and electrical resistivity. The dislocation density is determined from the electrical resistivity after AM, accounting for effects of phase fraction and phase composition.

Figure 1:
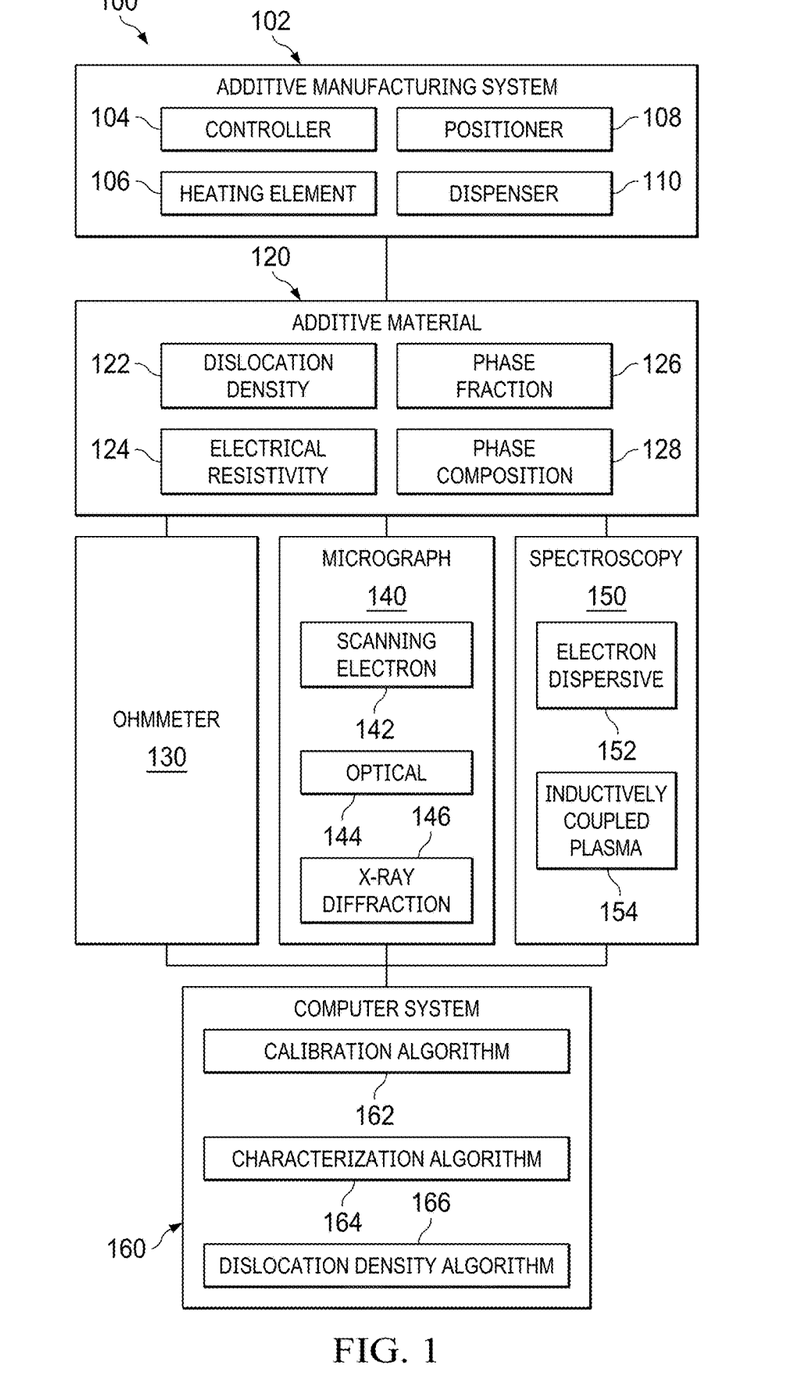
FIG. 1 is a block diagram illustrating a material strength assessment system for additive material in accordance with an illustrative embodiment.

FIG. 1 is a block diagram illustrating a material strength assessment system for additive material in accordance with an illustrative embodiment. System 100 comprises an additive manufacturing (AM) system 102 that performs AM processes on additive material 120. AM refers to a process of joining materials to make objects from three-dimensional model data. This is often performed, but not necessarily, in a layer-by-layer fashion. Some examples of AM include three-dimensional (3-D) printing, rapid prototyping, and directly digital manufacturing (DDM).

Controller 104 might prepare the digital data that characterizes a 3-D object for printing and control the operation of the AM system 102. In the present example, controller 104 is located inside AM system 102 but can also be outside of AM system 102 and communicate over a wire and/or using wireless communications. Control functionality can also be spread across units, and not all control functionality may be within AM system 102. For example, a separate unit, such as a personal computer or workstation, or a processing unit within a supply source such as a cartridge may provide some control or data storage capability.

Heating element 106 provides the heat for the thermal cycling of the AM processes. The heat provided by heating element 106 is sufficient to place the additive material 120 in a flowable state for the AM processes.

Positioner 108, or other suitable movement device, controls the movement and position of the dispenser head 110 during extrusion of the additive material 120 during AM processing.

The additive material 120 possesses several properties that can change over the course of repeated, rapid heating and cooling thermal cycles during AM processes. The properties include, among others, dislocation density 122, electrical resistivity 124, phase fraction 126, and phase composition 128. These properties, and their response to thermal cycling, will depend on the material in question. In an embodiment, the additive material 120 is titanium or a titanium alloy.

Phase fraction 126 describes the relative amount of different phases present in the additive material 120. For example, the titanium alloy Ti-6Al-4V has two phases, alpha and beta. Alloys generally do not have a single melting point but instead melt over a range of temperatures. The alpha phase is characterized as a solid solution in which some atoms of a first element are dissolved in a second element. Conversely, the beta phase is a solid solution in which some atoms of the second element are dissolved in the first element.

Phase composition 128 describes the individual chemical composition of each phase. The alpha phase has one chemical composition, and the beta phase has another. The overall average is the "chemical composition" of the alloy.

The different phases of the additive material 120 have different electrical resistivity values, which are also sensitive to chemistry.

Electrical resistivity 124 can be measured with an ohmmeter 130, which might be, e.g., a four-point contact probe ohmmeter. Phase fraction can be determined using a micrograph 140 such as, e.g., scanning electron micrograph 142, optical micrograph 144, or x-ray diffraction 146. Phase composition 128 can be determined using spectroscopy 150, which might be, e.g., electron dispersive spectroscopy 152 or inductively coupled plasma spectroscopy 154.

The ohmmeter 130, micrograph 140, and spectroscopy 150 can be controlled and analyzed by computer system 160. Computer system 160 comprises a calibration algorithm 162, a characterization algorithm 164, and a dislocation algorithm 166. Phase fraction and chemical composition of the phases are first assessed to develop a calibration curve by calibration algorithm 162 for the additive material 120 at a near constant level of dislocation density. This can be achieved by heat treating the material to reduce the dislocation density to a specified minimum value that contributes a negligible contribution to the strength of the material. The variation of phase content (alpha and beta) can be assessed along with the individual chemical elements that can have small influences on electrical resistivity, independent of dislocation density. Baseline calibration can also create a factor to assess vacancy and stacking faults as well if their contribution is significant and exceeds a specified threshold.

To assess the additive material after it has undergone AM thermal cycling it is characterized by characterization algorithm 164 for phase fraction, chemical composition (phase specific and global), and electrical resistivity. This characterization can be performed on a per specimen basis or on a broader scale where the bounds or distribution is assessed for a range of material. Phase fraction can be determined through a variety of techniques, depending on the length scale and resolution required, including, but not limited to measurements from scanning electron micrographs 142, optical micrographs 144, and x-ray diffraction 146.

Phase composition can be determined through a variety of techniques as well, depending on the required resolution, including without limitation electron dispersive spectroscopy (EDS) 152 and inductively coupled plasma spectroscopy (ICP) 154.

Electrical resistivity can be determined by, but not limited to, the use of an ohmmeter, such as ohmmeter 130, with sufficient resolution to determine changes in resistivity related to the phase composition, chemistry, and dislocation density. In an embodiment, the ohmmeter 130 comprises a multi-point (e.g., 4-point) contact probe with which multiple measurements are taken to account for inherent variability of the probe.

From the characterization of the additive material 120 after undergoing AM cycling, the dislocation density algorithm 166 applies empirical relationships in the scientific literature to determine dislocation density. By comparing baseline resistivity to resistivity after AM thermal cycling, the contribution from dislocation density is ascertained. Utilizing calibration and characterization related to microstructure of the additive material 120 separates out the effects of variation in phase fraction and chemical composition due to variability of material characteristics that are unique to additively manufactured material.

The calibration algorithm 162, a characterization algorithm 164, and a dislocation algorithm 166 make computer system 160 transform a computer system into a special purpose computer system as compared to currently available general computer systems that do not have a means to perform dislocation density and strength assessment such as computer system 160 of FIG. 1.

Figure 2:
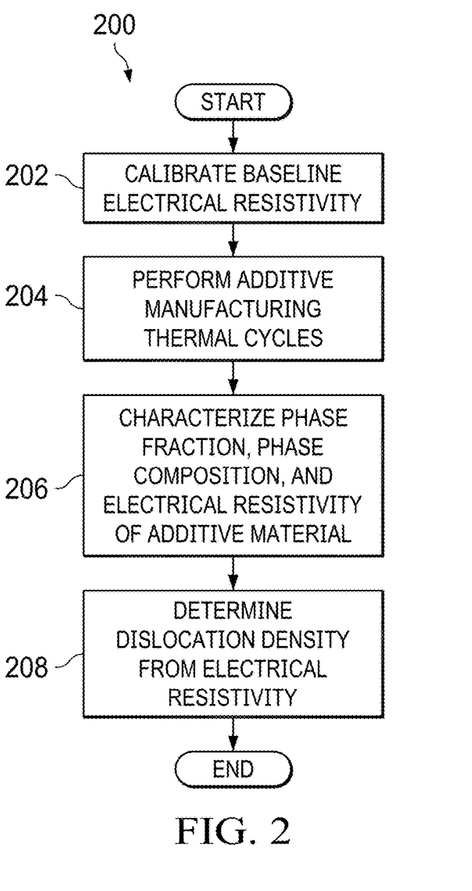
FIG. 2 is a flowchart illustrating a process flow for assessing dislocation density of additive materials in accordance with illustrative embodiments.

FIG. 2 is a flowchart illustrating a process flow for assessing dislocation density of additive materials in accordance with illustrative embodiments. Process 200 begins by calibrating baseline electrical resistivity of the additive material (step 202). This step is performed with the additive material at a near constant level of dislocation density. In an embodiment the resistivity is calibrated for additive material this heat treated to reduce dislocation density to a specified minimum value (see FIG. 3 below).

Figure 6:
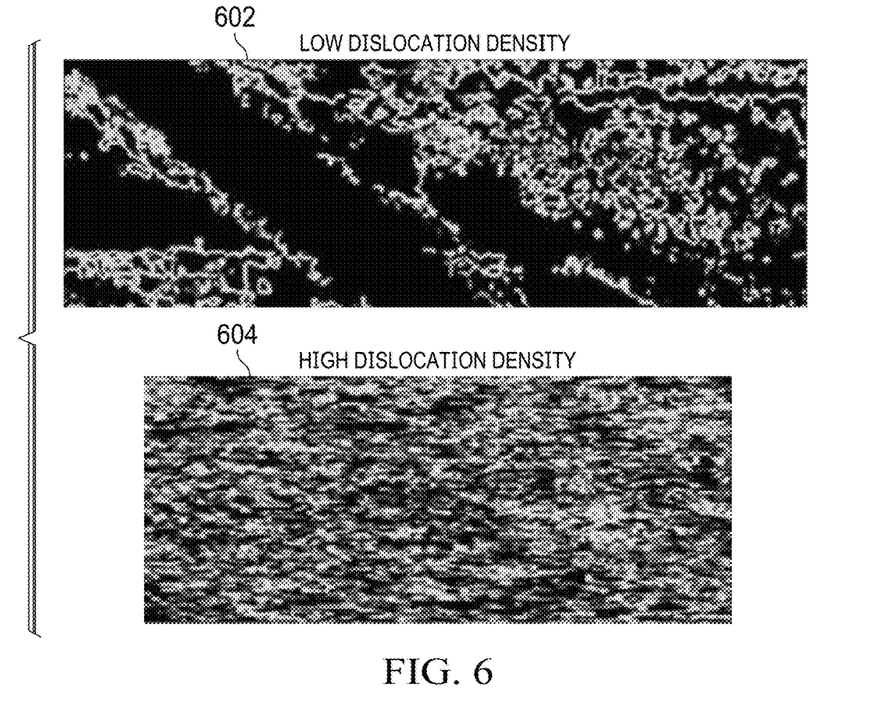
FIG. 6 illustrates dislocation density maps of titanium alloy after additive manufacturing in accordance with illustrative embodiments.

Once the baseline values have been calibrated, the additive material undergoes a number of heating and cooling cycles during AM (step 204). During the repeated, rapid heating and cooling thermal cycles, dislocations and dislocation density increase in the additive material, thereby increases the strength of the material. FIG. 6 illustrates dislocation density maps of titanium alloy based on micrographs for low dislocation density (map 602) and high dislocation density (graph 604).

The increase in dislocation density of a multi-phase additive material such as titanium alloy is analogous to increased dislocation in wrought materials, but in this case the dislocations are produced by thermal cycling instead of mechanical folding or rolling.

After the AM process is finished, the additive material is characterized for phase fraction, phase composition, and electrical resistivity (step 206).

Process 200 then determines the dislocation density of the additive material after AM according to electrical resistivity, accounting for effects of phase fraction and phase composition determined by characterization (step 208). The calibration before AM and characterization after AM allow the effects of changes in phase content and chemical composition on electrical resistivity to be separated out of the results.

Figure 3:
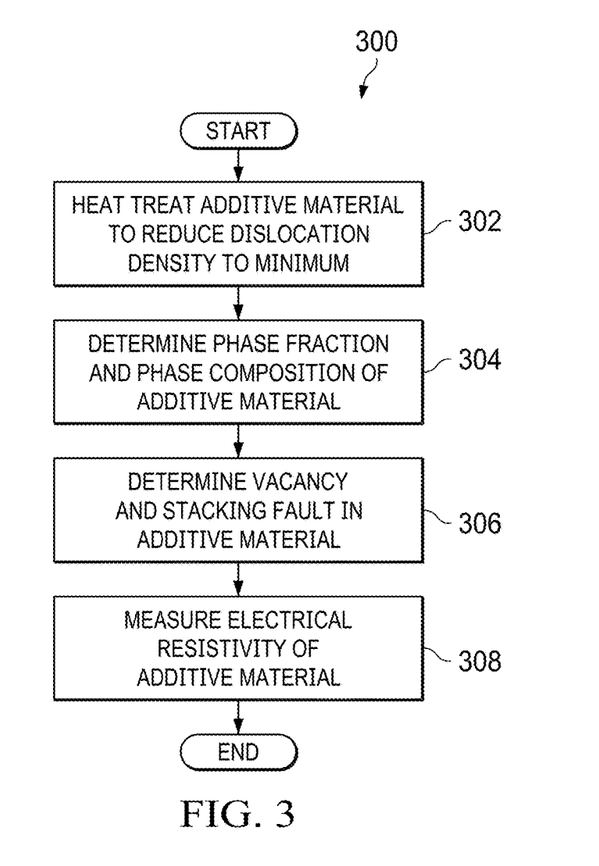
FIG. 3 is a flowchart illustrating the process flow for calibrating baseline electrical resistivity of additive materials in accordance with illustrative embodiments.

FIG. 3 is a flowchart illustrating the process flow for calibrating baseline electrical resistivity of additive materials in accordance with illustrative embodiments. Process 300 details the process of calibrating baseline curves in step 202 in FIG. 2. The sequence of steps shown in FIG. 3 is chosen for ease of illustration, but the steps can occur in different orders.

To minimize the influence of dislocation density on material strength, the additive material is heat treated to reduce dislocation density to a specified minimum value (step 302).

With the additive material at a near constant level of dislocation density, process 300 determines phase fraction and phase composition in the additive material (step 304). This step allows the electrical resistivity baseline to be established as a function of phase fraction and phase composition.

Process 300 might also comprise determining vacancy and stacking fault contributions to electrical resistivity if significant (step 306).

With the initial characterization in place, the electrical resistivity of the additive material is measured to establish the baseline value (step 308).

Figure 4:
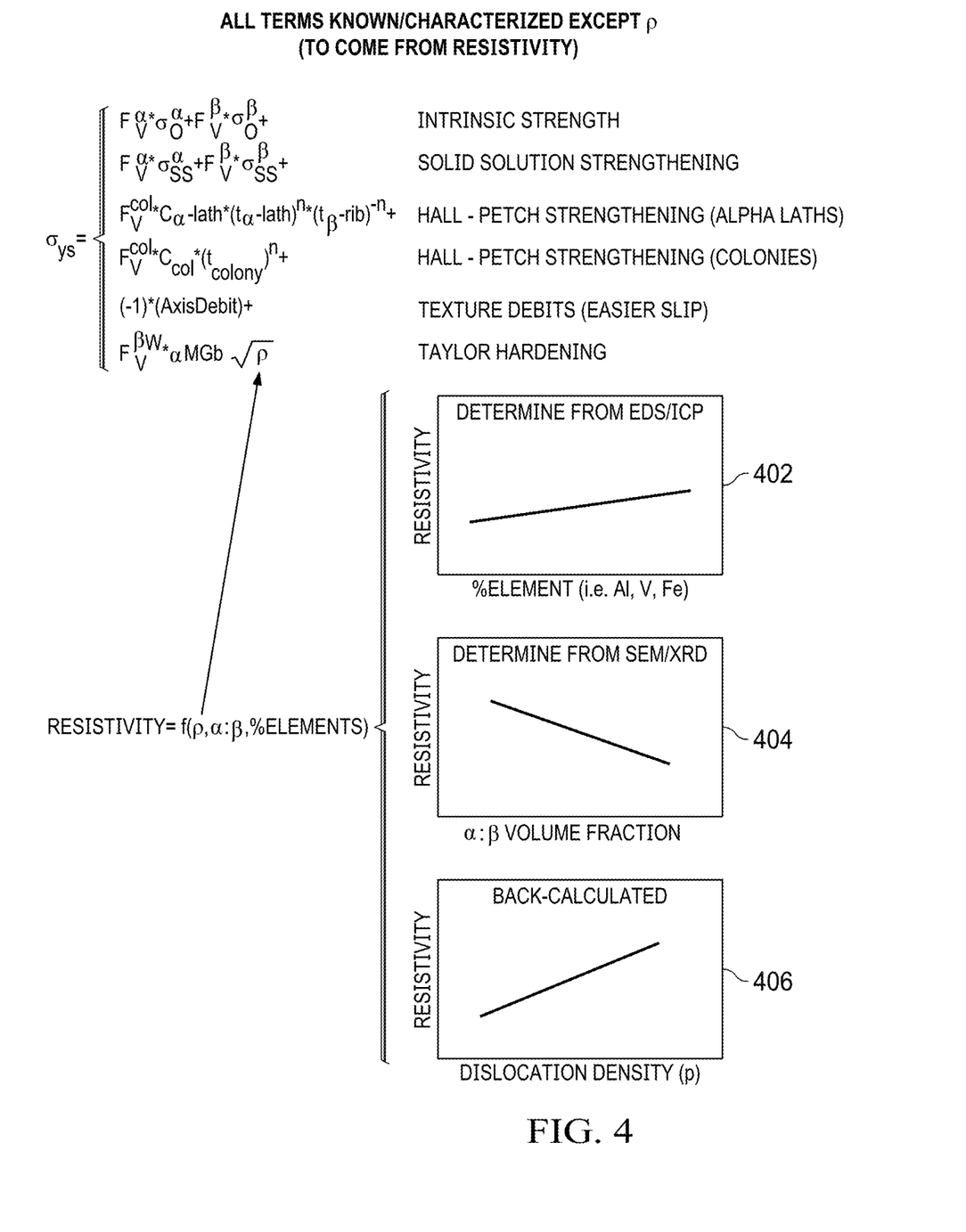
FIG. 4 illustrates the process of using dislocation density in calculating material strength of titanium alloy in accordance with an illustrative embodiment.
Figure 7:
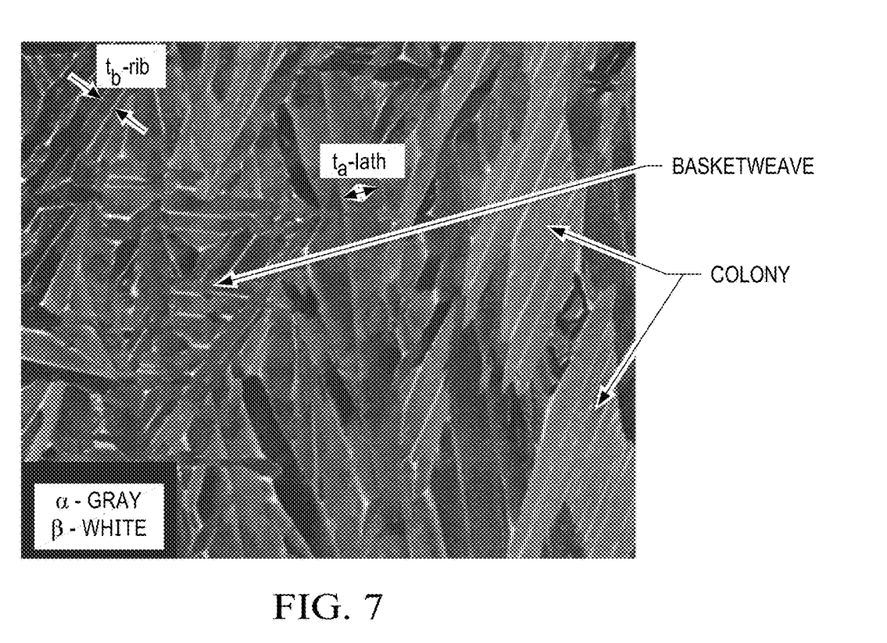
FIG. 7 illustrates a micrograph of titanium alloy microstructure after additive manufacturing in accordance with illustrative embodiments.

FIG. 4 illustrates the process of using dislocation density in calculating material strength of titanium alloy in accordance with an illustrative embodiment. Material strength can be predicted based on several physical parameters. For AM produced Ti-6Al-4V, the general equation for predicting strength is given in Equation 1 below.

$$\sigma_{ys} = \begin{cases} F_V^\alpha \cdot \sigma_O^\alpha + F_V^\beta \cdot \sigma_O^\delta + & \text{Intrinsic Strength} \\ F_V^\alpha \cdot \sigma_{SS}^\alpha + F_V^\beta \cdot \sigma_{SS}^\beta + & \text{Solid Solution Strengthening} \\ F_V^{col} \cdot C_{\alpha-lath} \cdot (t_{\alpha-lath})^n \cdot & \\ (t_{\beta-rib})^{-n} + & \text{Hall-Petch Strengthening (alpha laths)} \\ F_V^{col} \cdot C_{col} \cdot (t_{colony})^n + & \text{Hall-Petch Strenghening (colonies)} \\ (-1) \cdot (AxisDebit) + & \text{Texture Debits (easier slip)} \\ F_V^{BW} \cdot \alpha MGb\sqrt{\rho} & \text{Taylor Hardening} \end{cases} \quad \text{Eq. 1}$$

where $\sigma_o$ is the intrinsic strength of the material, $\sigma_{ss}$ is the intrinsic strength of solid solution, $F_V$ represents volume fraction of the designated phase/microstructure, $C_i$ represents prefactors for certain terms, $t_{feature}$ is the thickness of specific features within the microstructure (i.e. the α-laths, β-ribs, and colony scale factor) (see FIG. 7), α is the prefactor term, M is the Taylor factor, G is the shear modulus, and ρ is the dislocation density.

The parameters in Equation 1 are generally well known and characterized empirically in the art, except for the dislocation density, ρ. As explained above, current methods for determining dislocation density in additive materials are expensive, destructive, time consuming, and not suited to rapid qualification in a manufacturing environment. The illustrative embodiments provide a cost-effective method of using electrical resistivity of the additive material to determine this value and its strengthening contribution as part of an assessment represented in Equation 1.

As shown in FIG. 4, resistivity is a function of dislocation density, ρ, α:β volume fraction, and percentage of elements in the alloy. Graph 402 illustrates resistivity as a function of the percentage of elements (e.g., Al, V, Fe) determined from, e.g., EDS/ICP. Graph 404 illustrates resistivity as a function of phase volume fraction as determined from, e.g., scanning electron microscopy (SEM) or X-ray powder diffraction (XRD). By establishing these functions, the value for dislocation density can be back-calculated from resistivity during calibration and characterization in steps 202 and 206 in FIG. 2, as shown in graph 406. The missing value for p can then be provided for the Taylor hardening portion of the general assessment Equation 1.

Figure 5:
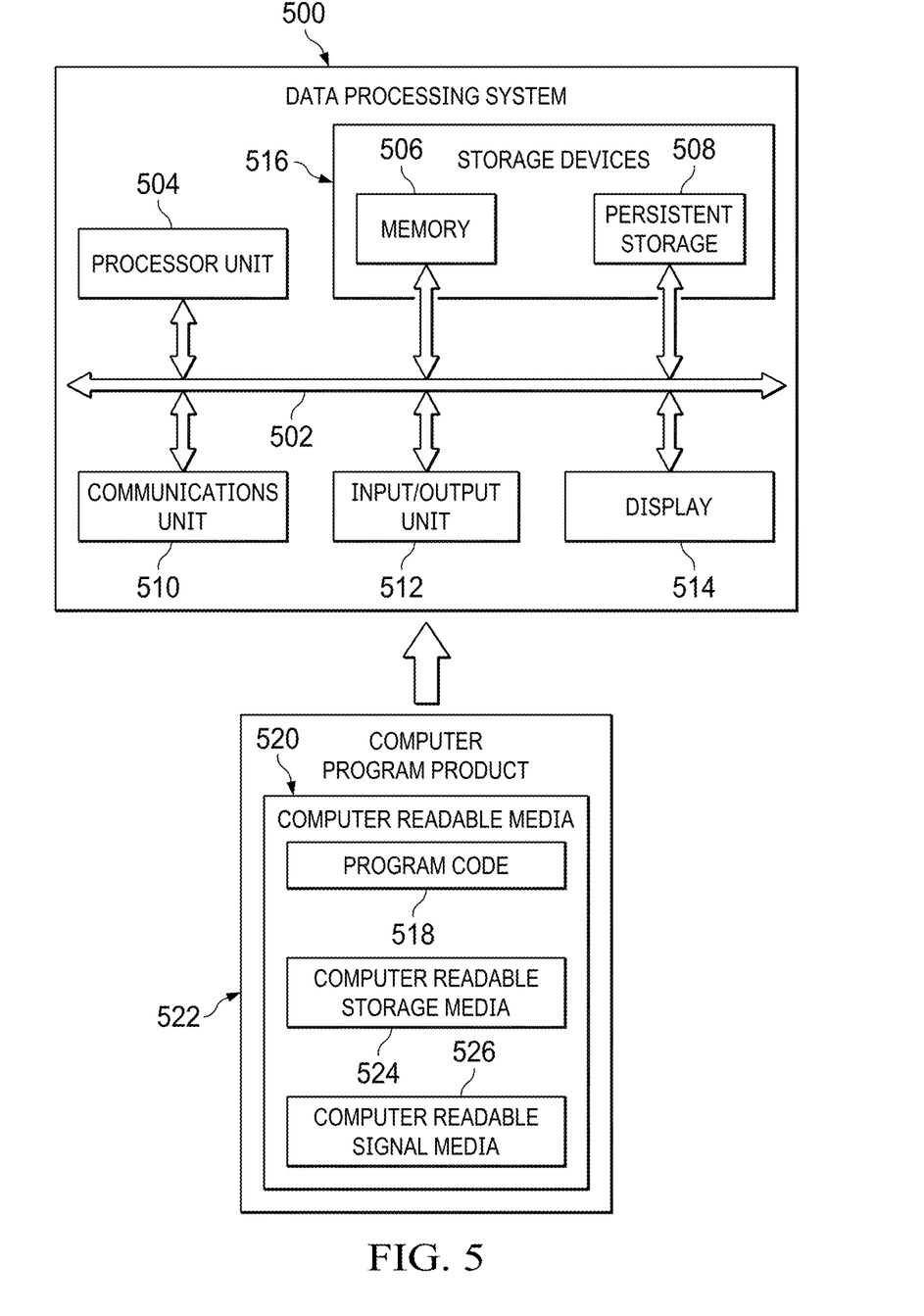
FIG. 5 is an illustration of a block diagram of a data processing system in accordance with an illustrative embodiment.

Turning now to FIG. 5, an illustration of a block diagram of a data processing system is depicted in accordance with an illustrative embodiment. Data processing system 500 may be used to implement one or more computers such as computer system 160 in FIG. 1 configured to carry out the computational steps illustrated in FIGS. 2-4. In this illustrative example, data processing system 500 includes communications framework 502, which provides communications between processor unit 504, memory 506, persistent storage 508, communications unit 510, input/output unit 512, and display 514. In this example, communications framework 502 may take the form of a bus system.

Processor unit 504 serves to execute instructions for software that may be loaded into memory 506. Processor unit 504 may be a number of processors, a multi-processor core, or some other type of processor, depending on the particular implementation. In an embodiment, processor unit 504 comprises one or more conventional general purpose central processing units (CPUs). In an alternate embodiment, processor unit 504 comprises a number of graphical processing units (CPUs).

Memory 506 and persistent storage 508 are examples of storage devices 516. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 516 may also be referred to as computer-readable storage devices in these illustrative examples. Memory 516, in these examples, may be, for example, a random access memory or any other suitable volatile or non-volatile storage device. Persistent storage 508 may take various forms, depending on the particular implementation.

For example, persistent storage 508 may contain one or more components or devices. For example, persistent storage 508 may be a hard drive, a flash memory, a rewritable optical disk, a rewritable magnetic tape, or some combination of the above. The media used by persistent storage 508 also may be removable. For example, a removable hard drive may be used for persistent storage 508. Communications unit 510, in these illustrative examples, provides for communications with other data processing systems or devices. In these illustrative examples, communications unit 510 is a network interface card.

Input/output unit 512 allows for input and output of data with other devices that may be connected to data processing system 500. For example, input/output unit 512 may provide a connection for user input through at least one of a keyboard, a mouse, or some other suitable input device. Further, input/output unit 512 may send output to a printer. Display 514 provides a mechanism to display information to a user.

Instructions for at least one of the operating system, applications, or programs may be located in storage devices 516, which are in communication with processor unit 504 through communications framework 502. The processes of the different embodiments may be performed by processor unit 504 using computer-implemented instructions, which may be located in a memory, such as memory 506.

These instructions are referred to as program code, computer-usable program code, or computer-readable program code that may be read and executed by a processor in processor unit 504. The program code in the different embodiments may be embodied on different physical or computer-readable storage media, such as memory 506 or persistent storage 508.

Program code 518 is located in a functional form on computer-readable media 520 that is selectively removable and may be loaded onto or transferred to data processing system 500 for execution by processor unit 504. Program code 518 and computer-readable media 520 form computer program product 522 in these illustrative examples. In one example, computer-readable media 520 may be computer-readable storage media 524 or computer-readable signal media 526.

In these illustrative examples, computer-readable storage media 524 is a physical or tangible storage device used to store program code 518 rather than a medium that propagates or transmits program code 518. Alternatively, program code 518 may be transferred to data processing system 500 using computer-readable signal media 526.

Computer-readable signal media 526 may be, for example, a propagated data signal containing program code 518. For example, computer-readable signal media 526 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 500 are not meant to provide architectural limitations to the manner in which different embodiments may be implemented. The different illustrative embodiments may be implemented in a data processing system including components in addition to or in place of those illustrated for data processing system 500. Other components shown in FIG. 5 can be varied from the illustrative examples shown. The different embodiments may be implemented using any hardware device or system capable of running program code 518.

FIG. 6 illustrates a micrograph of titanium alloy after additive manufacturing in accordance with illustrative embodiments.

FIG. 7 illustrates dislocation density maps of titanium alloy after additive manufacturing in accordance with illustrative embodiments.

As used herein, the phrase "a number" means one or more. The phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category. As used herein, the term "substantially" or "approximately" when used with respect to measurements is determined by the ordinary artisan and is within acceptable engineering tolerances in the regulatory scheme for a given jurisdiction, such as but not limited to the Federal Aviation Administration Federal Aviation Regulations.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. The steps shown in the flowchart might occur in a different order than the specific sequence of blocks shown.

The description of the different illustrative examples has been presented for purposes of illustration and description, and is not intended to be exhaustive or limited to the examples in the form disclosed. Many modifications and variations will be apparent to those of ordinary skill in the art. Further, different illustrative examples may provide different features as compared to other desirable examples.

The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A computer-implemented method of assessing material strength for additive manufacturing, the method comprising:
calibrating, by a number of processors, a baseline electrical resistivity of a multi-phase additive material for a set dislocation density as a function of phase fraction and phase composition, wherein individual phases of the multi-phase additive material have different electrical resistivity values;
characterizing, by a number of processors, the multi-phase additive material for phase fraction, phase composition, and electrical resistivity after the multi-phase additive material has undergone a number of heating and cooling cycles during additive manufacturing; and
determining, by a number of processors, dislocation density of the multi-phase additive material according to electrical resistivity after additive manufacturing, accounting for effects of phase fraction and phase composition determined by characterization.

2. The method of claim 1, wherein baseline electrical resistivity is calibrated for the multi-phase additive material that is heat treated to reduce dislocation density to a specified minimum value.

3. The method of claim 1, wherein calibrating baseline electrical resistivity further comprises determining phase fraction and phase composition in the multi-phase additive material.

4. The method of claim 1, wherein calibrating baseline electrical resistivity further comprises determining vacancy and stacking fault contributions to electrical resistivity.

5. The method of claim 1, wherein phase fraction of the multi-phase additive material is determined using at least one of:
scanning electron micrograph;
optical micrograph; or
x-ray diffraction.

6. The method of claim 1, wherein phase composition of the multi-phase additive material is determined using at least one of:
electron dispersive spectroscopy; or
inductively coupled plasma spectroscopy.

7. The method of claim 1, wherein resistivity is determined with a multi-point contact probe ohmmeter.

8. The method of claim 1, wherein the multi-phase additive material comprises titanium alloy.

9. A system for assessing material strength for additive manufacturing, the system comprising:
a bus system;
a storage device connected to the bus system, wherein the storage device stores program instructions; and
a number of processors connected to the bus system, wherein the number of processors execute the program instructions to:
calibrate a baseline electrical resistivity of a multi-phase additive material for a set dislocation density as a function of phase fraction and phase composition, wherein individual phases of the multi-phase additive material have different electrical resistivity values;
characterize the multi-phase additive material for phase fraction, phase composition, and electrical resistivity after the multi-phase additive material has undergone a number of heating and cooling cycles during additive manufacturing; and determine dislocation density of the multi-phase additive material according to electrical resistivity after additive manufacturing, accounting for effects of phase fraction and phase composition determined by characterization.

10. The system of claim 9, wherein baseline electrical resistivity is calibrated for the multi-phase additive material that is heat treated to reduce dislocation density to a specified minimum value.

11. The system of claim 9, wherein instructions executed by the processors for calibrating baseline electrical resistivity further comprise instructions to determine phase fraction and phase composition in the multi-phase additive material.

12. The system of claim 9, wherein instructions executed by the processors for calibrating baseline electrical resistivity further comprise instructions to determine vacancy and stacking fault contributions to electrical resistivity.

13. The system of claim 9, wherein phase fraction of the multi-phase additive material is determined using at least one of:
scanning electron micrograph;
optical micrograph; or
x-ray diffraction.

14. The system of claim 9, wherein phase composition of the multi-phase additive material is determined using at least one of:
electron dispersive spectroscopy; or
inductively coupled plasma spectroscopy.

15. The system of claim 9, further comprising a multi-point contact probe ohmmeter configured to determine resistivity.

16. The system of claim 9, wherein the multi-phase additive material comprises titanium alloy.

17. A computer program product for assessing material strength for additive manufacturing, the computer program product comprising:
a non-volatile computer readable storage medium having program instructions embodied therewith, the program instructions executable by a number of processors to cause a computer to perform the steps of:
calibrating a baseline electrical resistivity of a multi-phase additive material for a set dislocation density as a function of phase fraction and phase composition, wherein individual phases of the multi-phase additive material have different electrical resistivity values;
characterizing the multi-phase additive material for phase fraction, phase composition, and electrical resistivity after the multi-phase additive material has undergone a number of heating and cooling cycles during additive manufacturing; and
determining dislocation density of the multi-phase additive material according to electrical resistivity after additive manufacturing, accounting for effects of phase fraction and phase composition determined by characterization.

18. The computer program product of claim 17, wherein baseline electrical resistivity is calibrated for the multi-phase additive material that is heat treated to reduce dislocation density to a specified minimum value.

19. The computer program product of claim 17, wherein the instructions for calibrating baseline electrical resistivity further comprise instructions for determining phase fraction and phase composition in the multi-phase additive material.

20. The computer program product of claim 17, wherein the instructions for calibrating baseline electrical resistivity further comprise instructions for determining vacancy and stacking fault contributions to electrical resistivity.

* * * * *